R. S. WILLIAMS.

Gold-Foil for Dentists' Use.

No. 5,846. Reissued April 21, 1874.

Witnesses:

H. C. Mattenberg

C. Johnson

Inventor:

Richard S. Williams per Geo. Gifford

Atty

AM. PHOTO-LITHOGRAPHIC Co. N. Y. (OSBORNE'S PROCESS)

UNITED STATES PATENT OFFICE.

RICHARD S. WILLIAMS, OF NEW YORK, N. Y.

IMPROVEMENT IN GOLD-FOIL FOR DENTISTS' USE.

Specification forming part of Letters Patent No. 126,242, dated April 30, 1872; reissue No. 5,846, dated April 21, 1874; application filed March 17, 1874.

*To all whom it may concern:*

Be it known that I, RICHARD S. WILLIAMS, of the city, county, and State of New York, have invented a new and useful Improvement in Preparing Gold for Dental Purposes; and that the following is a full, clear, and exact description of the same, reference being had to the accompanying drawings and to the letters of reference marked thereon.

This invention relates to a new preparation of gold-foil for dental purposes, by means of which the gold may be used for purposes for which it is not otherwise well adapted. It consists in rolling the foil into cylinders, or forming it in other shape so that the several folds or layers of the foil will lie in the same plane, or be, practically, parallel with each other. The foil thus formed up is cut to the required size and shape without consolidating or condensing the ends at the place where it has been cut.

Figure 1:
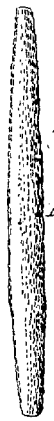
Figure 2:
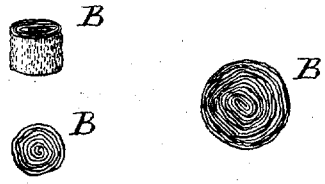
Figure 3:
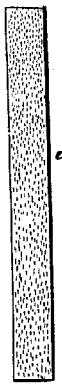
Figure 4:
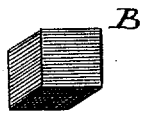
Figure 5:
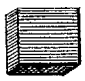

In the accompanying sheet of drawings, Figure 1 represents a roll or cylinder, marked A, formed of one or more sheets or layers of gold-foil; Fig. 2, sections of cylinder; Fig. 3, foil in parallelogrammic form, and Figs. 4 and 5 cubes and blocks of foil.

Similar letters of reference indicate corresponding parts in the several figures.

The chief object attained by dental gold made in accordance with my invention is, that the gold may be easily and readily compressed into the cavities of the teeth, so that it will enter the smallest cavity, and, being thoroughly non-elastic, remains where it is placed, and, at the same time, permits the pieces of gold-filling, as it is added piece by piece, to adhere one to the other, making a solid, or nearly solid, filling.

To prepare my gold, I first take what is commonly known as corrugated gold-foil, either part of a sheet, or one or more whole sheets, according to the quantity required, and I then loosely roll it into a uniform cylinder, or carefully form it up into square or cubical form, taking care to keep the several laminæ in the same plane, or parallel to each other. In this way the inner folds do not adhere, and the cylinder or block of foil is thoroughly non-elastic and soft.

The foil being built up in the way above described, the edge of the last fold is warmed in a spirit-lamp, which will make it adhere to the fold immediately under it, keeping the foil in place. The foil is then cut to the required size and shape by a razor or other similar instrument with a keen edge, which is drawn with a light pressure across the foil. The foil being cut in this way, the edges will be found uncondensed; or, in other words, the several laminæ will be distinct and separate from each other.

I am aware that corrugated gold-foil may, by putting a number of sheets on top of each other, be cut into square blocks or pieces. I have prepared gold-foil in that way myself; but this plan requires a certain degree of adhesiveness between the sheets, else, when the gold is cut, the layers will separate, or the edges of the layers will be crushed together, and produce an objectionable degree of stiffn ss, which is avoided by my plan.

My invention has this advantage, that short cylinders and other forms of gold are produced which are extremely useful in filling teeth.

The gold-foil prepared as above described may be of the plain or uncorrugated foil; but it is difficult to cut the plain gold without crushing and consolidating the edges, and thereby, in a great measure, defeating the main object, which is to leave the pieces as soft as possible.

Dentists do not possess the instruments and other facilities for producing these short cylinders or blocks of corrugated gold foil, as required in their practice; nor have they usually the necessary time to spend in the operation. They desire to have the gold they use prepared in the most convenient and perfect form for the various uses to which they apply it.

Having thus described my invention, what I claim as new, and desire to secure by Letters Patent, is—

1. As an article of manufacture, the pellets B, formed of finely-indented gold-foil, coiled into a cylindrical form, and cut, as described, and for the purpose set forth.

2. Dental gold composed of several folds or laminæ of foil lying in the same plane, and the edges of the same unconsolidated with each other.

RICHD. S. WILLIAMS.

Witnesses:
H. L. WATTENBERG,
G. M. PLYMPTON.